United States Patent
Barfoot et al.

(10) Patent No.: US 12,285,507 B2
(45) Date of Patent: *Apr. 29, 2025

(54) DEPOSITION SYSTEM FOR HAIR

(71) Applicant: Conopco, Inc., Englewood Cliffs, NJ (US)

(72) Inventors: Richard Jonathan Barfoot, Wirral (GB); Heather Clarkson, Wirral (GB); Michael James Cooke, Wirral (GB); Kelvin Brian Dickinson, Wirral (GB); Colin Christopher David Giles, Wirral (GB); Cesar Ernesto Mendoza Fernandez, Wirral (GB); Rongrong Zhou, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 678 days.

This patent is subject to a terminal disclaimer.

(21) Appl. No.: 17/414,181

(22) PCT Filed: Dec. 16, 2019

(86) PCT No.: PCT/EP2019/085377
§ 371 (c)(1),
(2) Date: Jun. 15, 2021

(87) PCT Pub. No.: WO2020/127070
PCT Pub. Date: Jun. 25, 2020

(65) Prior Publication Data
US 2022/0040062 A1    Feb. 10, 2022

(30) Foreign Application Priority Data

Dec. 19, 2018  (EP) .................................. 18213920

(51) Int. Cl.
| | |
|---|---|
| *A61K 8/11* | (2006.01) |
| *A61K 8/34* | (2006.01) |
| *A61K 8/37* | (2006.01) |
| *A61K 8/41* | (2006.01) |
| *A61K 8/898* | (2006.01) |
| *A61Q 5/12* | (2006.01) |

(52) U.S. Cl.
CPC ................ *A61K 8/11* (2013.01); *A61K 8/342* (2013.01); *A61K 8/416* (2013.01); *A61K 8/898* (2013.01); *A61Q 5/12* (2013.01); *A61K 8/375* (2013.01); *A61K 2800/412* (2013.01); *A61K 2800/56* (2013.01); *A61K 2800/591* (2013.01)

(58) Field of Classification Search
CPC .......... A61K 8/11; A61K 8/342; A61K 8/375; A61K 8/416; A61K 8/898; A61K 2800/412; A61K 2800/56; A61K 2800/591; A61Q 5/12
See application file for complete search history.

(56) References Cited

U.S. PATENT DOCUMENTS

| | | |
|---|---|---|
| 4,954,335 A | 9/1990 | Janchipraponvej |
| 4,981,845 A | 1/1991 | Pereira |
| 9,138,385 B2 | 9/2015 | Dahl et al. |
| 9,289,630 B2 | 3/2016 | Lee et al. |
| 2003/0147842 A1 | 8/2003 | Restle et al. |
| 2003/0157049 A1 | 8/2003 | Gawtrey et al. |
| 2006/0034792 A1 | 2/2006 | Lazzeri et al. |
| 2009/0005462 A1 | 1/2009 | Gunn et al. |
| 2012/0148644 A1 | 6/2012 | Popplewell et al. |
| 2013/0259817 A1 | 10/2013 | Uehara et al. |
| 2013/0330292 A1 | 12/2013 | Lei et al. |
| 2014/0072524 A1 | 3/2014 | Krueger |
| 2014/0246041 A1 | 9/2014 | Krueger |
| 2014/0286889 A1 | 9/2014 | Koehle et al. |
| 2016/0081907 A1 | 3/2016 | Schwab et al. |
| 2016/0083333 A1 | 3/2016 | Schwab et al. |
| 2016/0106663 A1 | 4/2016 | Gulbin |
| 2017/0143606 A1 | 5/2017 | Giesen |
| 2017/0252274 A1 | 9/2017 | Lei et al. |
| 2018/0064619 A1 | 3/2018 | Brun et al. |
| 2018/0110699 A1 | 4/2018 | Conway et al. |

FOREIGN PATENT DOCUMENTS

| | | |
|---|---|---|
| DE | 2011086633 | 5/2013 |
| DE | 102014224802 | 10/2015 |
| DE | 102015223028 | 6/2016 |
| DE | 102011087906 | 6/2023 |
| EP | 0530974 | 3/1993 |
| EP | 1257353 | 11/2002 |

(Continued)

OTHER PUBLICATIONS

Varisoft EQ100 Brochure—Evonik Industries AG, 2014, pp. 1-4. (Year: 2014).*
IPRP1 in PCTEP2019084381; Jul. 1, 2021; World Intellectual Property Org. (WIPO).
Yang et al.; Eco-Friendly, Vegetable-base Esterquat from Evonik; Happi; Dec. 1, 2009; pp. 62-65, XP055077918; Retrieved from the Internet: URL:http://personal-care.evonik.com/product/personal-care/en/media-center/downloads/publications/Documents/happi-varisoft-eq-65.pdf.
Ernest W. Flick; Cosmetic and Toiletry Formulations (Second Edition); .; 1992; pp. 442, XP002797540; vol. 2; Retrieved from the Internet: URL:http://www.anme.com.mx/libros/Cosmetic%20and%20Toiletry%20Formulations.pdf.
IPRP1 in PCTEP2019086032; Jul. 1, 2021; World Intellectual Property Org. (WIPO).
IPRP1 in PCTEP2019085377; Jul. 1, 2021; World Intellectual Property Org. (WIPO).

(Continued)

*Primary Examiner* — Kyung S Chang
(74) *Attorney, Agent, or Firm* — Byrne Poh LLP; Nina R. Horan

(57) ABSTRACT

A hair treatment composition comprising: a) a conditioning base comprising: i) a cationic conditioning surfactant having from 16 to 32 carbon atoms; ii) a fatty alcohol having from 8 to 22 carbon atoms; and b) from 0.1 to 10 wt % of a microcapsule in which a core comprising benefit agent is encapsulated in a polymeric shell; and (c) from 0.1 to 5 wt % of a diesterquat, provides improved deposition of microcapsules and delivery of benefit agent to hair surfaces.

16 Claims, No Drawings

(56) References Cited

FOREIGN PATENT DOCUMENTS

| | | |
|---|---|---|
| EP | 1854448 | 11/2007 |
| EP | 2022465 | 2/2009 |
| EP | 2022476 | 2/2009 |
| EP | 2216010 | 8/2010 |
| EP | 2623091 | 8/2013 |
| EP | 2355904 | 1/2017 |
| EP | 3403640 | 11/2018 |
| FR | 3026297 | 4/2016 |
| FR | 3059900 | 6/2018 |
| JP | 2004508313 | 3/2004 |
| WO | WO9629980 | 10/1996 |
| WO | WO9631188 | 10/1996 |
| WO | WO9962492 | 12/1999 |
| WO | WO0139735 | 6/2001 |
| WO | WO0162376 | 8/2001 |
| WO | WO0219976 | 3/2002 |
| WO | WO03037280 | 5/2003 |
| WO | WO2005102261 | 11/2005 |
| WO | WO2009016555 | 2/2009 |
| WO | WO2009074464 | 6/2009 |
| WO | WO2010079468 | 7/2010 |
| WO | WO2011072853 | 6/2011 |
| WO | WO2011107432 | 9/2011 |
| WO | WO2012084866 | 6/2012 |
| WO | WO2012119810 | 9/2012 |
| WO | WO2012138690 | 10/2012 |
| WO | WO2013072161 A3 | 5/2013 |
| WO | WO2014016351 | 1/2014 |
| WO | WO2014016352 | 1/2014 |
| WO | WO2014016353 | 1/2014 |
| WO | WO2014016354 | 1/2014 |
| WO | WO2014056962 | 4/2014 |
| WO | WO2015189309 | 12/2015 |
| WO | WO2016061435 | 4/2016 |
| WO | WO2016061439 | 4/2016 |
| WO | WO2016061440 | 4/2016 |
| WO | WO2016151139 | 9/2016 |
| WO | WO2017071915 | 5/2017 |
| WO | WO2018229175 | 12/2018 |

OTHER PUBLICATIONS

Search Report and Written Opinion in EP18213920; Mar. 1, 2019.
Search Report and Written Opinion in EP18213912; Mar. 27, 2019.
Search Report and Written Opinion in EP18214091; Jun. 28, 2019.
Search Report and Written Opinion in PCTEP2019085377; Feb. 13, 2020.
Evonik; Varisoft EQ100, Product Data record; Feb. 18, 2019; pp. 1-5, XP055663875; Edition 8; Germany.
Search Report and Written Opinion in PCTEP2019086032; Feb. 11, 2020.
Search Report and Written Opinion in PCTEP2019084381; Feb. 28, 2020.
Flick, Ernest, W, p. 442, 1992 Retrieved from Internet, http//www.anme.com.mx/libros/cosmetic%20and%20Toiletry%20formulations; Feb. 7, 2020.
Yang, Brian; et al, Retrieved from Internet on Sep. 5, 2013; pp. 62-65; Dec. 1, 2009.
Evonik, "Personal Care, Catalog of Products", (2015), 50 pages, Retrieved from the Internet, URL: https://www.kemiropa.com.tr/tr/wp-content/uploads/2018/05/PDF-22.pdf.
GNPD Database (Online) Mintel; Curl Conditioner; Madam C.J. Walker Beauty Culture Frizz Fighting Coconut & Moringa Oils; Apr. 2016; pp. 1-5; Record ID 3904857; Japan.
GNPD Database (Online) Mintel; Conditioner; Creightons Sunshine Blonde Tone Correcting; Oct. 2016; pp. 1-4, Record ID 4317989; Japan.
GNPD Database (Online) Mintel; Accelerator Conditioner; Botica Commercial Farmaceutica; Sep. 2017; pp. 1-4, Record ID:5062001; Japan.
GNPD Database (Online) Mintel; Supreme Shine Conditioner; O Botica Nativa Spa Ameixa Brilhissimio; Nov. 2017; pp. 1-4, Record ID:524849; Japan.
GNPD Database (Online) Mintel; Conditioner; L'Occitane au Bresil Pataua Hidratacao Equilibrante; Apr. 2018; pp. 1-4; Record ID:5580633; Japan.
GNPD Database (Online) Mintel; Reconstruction Conditioner; O Boticario Match SOS Reconstrucao; Aug. 2018; pp. 1-3, Record ID 5919081; XP093107483; Brazil.
GNPD Database (Online) Mintel; Conditioner; Eudora Siage Solar; Nov. 2018; pp. 1-3, Record ID 6165335, XP093107481; Brazil.
Carechemicals; Cetearyl Alcohol (and) Dipalmitoylethyl Hydroxyethylmonium Methosulfate (and) Ceteareth-20; Dehyquart C 4046; Aug. 15, 2005; pp. 1-2; cognis.
Evonik Industries; Readily biodegradable ester quat with excellent conditioning performance; Varisoft EQ 65 Pellets; Feb. 2008; pp. 1-4.
GNPD Database (Online) Mintel; Hair Mask and Conditioner; Yenzah Repair One Minute; Nov. 2018; pp. 1-3, Record ID 6165295; Brazil.
GNPD Database (Online) Mintel; Perfume Hair Conditioner; Tonymoly; Dec. 2016; pp. 1-3, Record ID 4495637; Russian Federation.
Kosmetic; ein okonomisches Avivage-Compound; Dehyquart C 4046; Sep. 1995; pp. 1-5; Nr. VII/95.
Notice of Opposition in EP19817753 (EP3897543); Jun. 21, 2023; European Patent Office (EPO).
BASF; INCI: Distearoylethyl Hydroxyethylmonium Methosulfate (and) Cetearyl Alcohol; Dehyquart F 75 T; 2024; pp. 1-2.
Clariant; Enhancing hair strength; Genadvance Repair Product Sheet; 2019; pp. 1-16; Switzerland.
National Center for Biotechnology Information; Cetearyl alcohol; National Library of Medice Compound Summary; 2024; pp. 1-22; PubCehm CID 62238.
National Center for Biotechnology Information; Distearoylethyl hydroxyethylmonium methosulfate; National Library of Medicine Compound Summary; 2024; pp. 1-16; PubChem CID 21124016.
Nouryon Catalog Website; Dipalmitoylethyl Dimonium Chloride; Armocare VGH-70; 2024; pp. 1-4.
Soytrimonium chloride (CAS No. 61790-41-8; EC No. 263-134-0); Scientific Committee on Consumer Safety (SCCS); 2024; pp. 1-2.
U.S. Department of Health & Human Services; Dioleoylisopropyl Dimonium Methosulfate Y0I7EU4P4G; National Institutes of Health; 2024; pp. 1-4.
U.S. Department of Health & Human Services; Dipalmitoylethyl Dimonium Chloride equivalent to Armocare VGH 70; National Institutes of Health; 2024; pp. 1-3.

\* cited by examiner

DEPOSITION SYSTEM FOR HAIR

CROSS-REFERENCE TO RELATED APPLICATIONS

This application is a U.S. 371 National Stage Application of PCT International Application No. PCT/EP2019/085377, with international filing date of Dec. 16, 2019, which claims the benefit of and priority to European patent application No. 18213920.4 filed Dec. 19, 2018, the contents of which are incorporated herein by reference in their entireties.

FIELD OF THE INVENTION

The present invention relates to hair treatment compositions containing a diester quat and the use of these compositions to deposit microcapsules on hair surfaces.

BACKGROUND AND PRIOR ART

In personal care compositions such as hair conditioners, the deposition and delivery of benefit agents are often key drivers of product performance. For example, many of the conditioner products in the market today work to deliver benefits to hair by depositing benefit agents such as fragrance materials, silicones and damage repair actives onto the hair during the wash and care process.

Various technologies have been employed to enhance the delivery of benefit agents at the desired time. One widely used technology is encapsulation of the benefit agent in a protective coating such as a polymeric material. The polymeric material may protect the benefit agent, such as a fragrance material, from evaporation, reaction, oxidation or otherwise dissipating prior to use.

However, maximizing encapsulate deposition during a wash and care is a difficult task due to the rinse off nature of the compositions. When encapsulates are washed away, relatively high levels of encapsulated benefit agents may be needed in the composition to deliver the consumer desired benefit.

Accordingly, there is a need for a hair composition that provides an increased deposition of encapsulated benefit agents onto the hair or skin, without impairing other product attributes such as rheology, sensory and conditioning performance.

US2016081907 (Evonik) discloses hair formulations containing liquid ester quats and/or imidazolinium salts that are made stable for over a long term by the addition of carbomers or other polymers. US2016083333 discloses cosmetic formulations containing mixed ester quats for cosmetically treating keratin fibres.

DE102015223028 (Henkel) discloses a cosmetic composition for treating keratin fibers, containing in a cosmetic carrier, a) at least one specified esterquat in an amount of 0.01 to 20.0 weight %, based on the weight of the total composition, and b) at least a further different from a) cationic and/or cationizable compound in an amount of 0.01 to 20.0 weight %.

It has now been found that a combination of particular esterquats with a microcapsule in a hair treatment composition provides improved deposition of the microcapsule to hair.

Definition of the Invention

In a first aspect, the present invention provides a hair treatment composition comprising:
a) a conditioning base comprising:
  i) a cationic conditioning surfactant having from 16 to 32 carbon atoms;
  ii) a fatty alcohol having from 8 to 22 carbon atoms; and
b) from 0.1 to 10 wt % of a microcapsule in which a core comprising benefit agent is encapsulated in a polymeric shell;
wherein the composition further comprises:
  (c) from 0.1 to 5 wt % of a diesterquat.

In a second aspect the invention provides a method of treating hair comprising the step of applying the hair a composition of the first aspect of the invention.

In a third aspect the invention provides a use of a diesterquat to deposit a microcapsule comprising a core comprising benefit agent is encapsulated in a polymeric shell on hair.

GENERAL DESCRIPTION OF THE INVENTION

The Encapsulated Benefit Agent

The composition of the invention comprises microcapsules in which a core comprising benefit agent is encapsulated in a polymeric shell.

The microcapsules are preferably present in an amount of from 0.1 to 5% by weight of the total composition.

The term "benefit agent" in the context of this invention includes materials which can provide a benefit to the hair and/or the scalp as well as those materials which are beneficially incorporated into hair treatment compositions, such as aesthetic agents.

The benefit agent of the core of the microcapsule may suitably be selected from perfumes, cosmetic active ingredients such as antimicrobial agents, antidandruff agents, moisturisers, conditioning agents, sunscreening agents, physiological coolants and emollient oils; and mixtures thereof.

Preferably the benefit agent of the core of the microcapsule is selected from perfumes. A perfume normally consists of a mixture of a number of perfume materials, each of which has an odour or fragrance. The number of perfume materials in a perfume is typically 10 or more. The range of fragrant materials used in perfumery is very wide; the materials come from a variety of chemical classes, but in general are water-insoluble oils. In many instances, the molecular weight of a perfume material is in excess of 150, but does not exceed 300.

Examples of perfume materials for use in the invention include geraniol, geranyl acetate, linalol, linalyl acetate, tetrahydrolinalol, citronellol, citronellyl acetate, dihydromyrcenol, dihydromyrcenyl acetate, tetrahydromyrcenol, terpineol, terpinyl acetate, nopyl acetate, 2-phenyl-ethanol, 2-penylethyl acetate, benzyl alcohol, benzyl acetate, benzyl salicylate, styrallyl acetate, benzyl benzoate, amyl salicylate, dimethylbenzyl-carbinol, trichloromethylphenyl-carbinyl acetate, p-tert-butylcyclohexyl acetate, isononyl acetate, vetiveryl acetate, vetiverol, α-hexylcinnamaldehyde, 2-methyl-3-p-tert-butylpheyl)propanal, 2-methyl-3-(p-isopropylphenyl)propanal, 2-(p-tert-butylpheyl)propanal, 2,4-dimethyl-cyclohex-3-enyl-carboxaldehyde, tricyclodecenyl acetate, tricyclodecenyl propionate,4-(4-hydroxy-4-methylpentyl)-3-cyclohexenecarboxyaldehyde, 4-(4-methyl-3-pentenyl)-3-cyclohexenecarboxaldehyde, 4-acetoxy-3-pentyltetrahydropyran, 3-carboxymethyl-2-pentylcyclopentane, 2-n-heptylcyclopentanone, 3-methyl-2-pentyl-2-cyclopentenone, n-decanal, n-dodecanal, 9-decenol-1, phenoxyethyl isobutyrate, phenyl-acetaldehyde dimethyl-acetal, phenylacetaldehyde diethylacetal, geranyl nitrile, citronellyl nitrile, cedryl acetate, 3-isocamphylcyclohexanol, cedryl methyl ether, isolongifolanone, aubepine nitrile, aubepine, heliotropin, coumarin, eugenol, vanillin, diphenyl oxide, hydroxycitronellal, ionones, methylionones, isomethylionones, irones, cis-3-hexenol and esters thereof, indan musks, tetralin musks, isochroman musks, macrocyclic ketones, macrolactone musks, ethylene brassylate and mixtures thereof.

Optional further materials which may be included in the core of the microcapsule include dyes, pigments, preservatives and carriers.

The polymeric shell of the microcapsule may be prepared using interfacial polymerisation.

Interfacial polymerisation produces encapsulated shells from the reaction of at least one oil-soluble wall forming material present in the oil phase with at least one water-soluble wall forming material present in the aqueous phase. A polymerisation reaction between the two wall-forming materials occurs resulting in the formation of covalent bonds at the interface of the oil and aqueous phases to form the capsule wall.

Preferably the polymeric shell of the microcapsule is an aminoplast resin selected from polyurea formed by reaction of polyisocyanates with material selected from polyamines, polyimines or mixtures thereof.

Preferably, the microcapsules are activated by shear; that is to say they are broken by shear to release the contents.

A particularly preferred microcapsule has a polyurea shell, prepared as described in US2013/0330292 A1 and US2012/0148644 A1 and available from International Flavors & Fragrances Inc.

Advantageously the polymeric shell comprises at most 20 wt % of the weight of the microcapsules.

By modifying process conditions microcapsules of a desired size can be produced in known manner. The microcapsules typically have a mean diameter in the range 1 to 500 microns, preferably 1 to 300 microns, more preferably 1 to 50 microns and most preferably 1 to 10 microns. If necessary, the microcapsules as initially produced may be filtered or screened to produce a product of greater size uniformity.

In a typical composition according to the invention the level of microcapsules will generally range from 0.2 to 2%, and preferably ranges from 0.5 to 1.5% by weight based on the total weight of the composition.

The Cationic Conditioning Surfactant

Conditioner compositions will comprise a cationic conditioning surfactant, which is cosmetically acceptable and suitable for topical application to the hair.

Preferably, the cationic conditioning surfactants have the formula $N^+(R^1)(R^2)(R^3)(R^4)$, wherein $R^1$, $R^2$, $R^3$ and $R^4$ are independently ($C_1$ to $C_{30}$) alkyl or benzyl.

Preferably, one, two or three of $R^1$, $R^2$, $R^3$ and $R^4$ are independently ($C_4$ to $C_{30}$) alkyl and the other $R^1$, $R^2$, $R^3$ and $R^4$ group or groups are ($C_1$-$C_6$) alkyl or benzyl.

More preferably, one or two of $R^1$, $R^2$, $R^3$ and $R^4$ are independently ($C_6$ to $C_{30}$) alkyl and the other $R^1$, $R^2$, $R^3$ and $R^4$ groups are ($C_1$-$C_6$) alkyl or benzyl groups. Optionally, the alkyl groups may comprise one or more ester (—OCO— or —COO—) and/or ether (—O—) linkages within the alkyl chain. Alkyl groups may optionally be substituted with one or more hydroxyl groups. Alkyl groups may be straight chain or branched and, for alkyl groups having 3 or more carbon atoms, cyclic. The alkyl groups may be saturated or may contain one or more carbon-carbon double bonds (e.g., oleyl). Alkyl groups are optionally ethoxylated on the alkyl chain with one or more ethyleneoxy groups.

Suitable cationic conditioning-surfactants for use in conditioner compositions according to the invention include cetyltrimethylammonium chloride (CTAC), behenyltrimethylammonium chloride (BTAC), cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, dihydrogenated tallow dimethyl ammonium chloride (e.g., Arquad 2HT/75 from Akzo Nobel), cocotrimethylammonium chloride, PEG-2-oleammonium chloride and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in conditioners according to the invention is cetyltrimethylammonium chloride, available commercially, for example as GENAMIN CTAC, ex Hoechst Celanese. Another particularly useful cationic surfactant for use in conditioners according to the invention is behenyltrimethylammonium chloride, available commercially, for example as GENAMIN KDMP, ex Clariant. Preferably, the cationic surfactant is selected from cetyltrimethylammonium chloride and behenyltrimethylammonium chloride, most preferably behenyltrimethylammonium chloride.

Another example of a class of suitable cationic surfactants for use in the invention, either alone or together with one or more other cationic surfactants, is a combination of (i) and (ii) below:

(i) an amidoamine corresponding to the general formula (II):

$$R1CONH(CH2)mN(R2)R3 \qquad (II)$$

in which $R^1$ is a hydrocarbyl chain having 10 or more carbon atoms, $R^2$ and $R^3$ are independently selected from hydrocarbyl chains of from 1 to 10 carbon atoms, and m is an integer from 1 to about 10; and (ii) an acid.

As used herein, the term hydrocarbyl chain means an alkyl or alkenyl chain.

Preferred amidoamine compounds are those corresponding to formula (I) in which $R^1$ is a hydrocarbyl residue having from about 11 to about 24 carbon atoms, $R^2$ and $R^3$ are each independently hydrocarbyl residues, preferably alkyl groups, having from 1 to about 4 carbon atoms, and m is an integer from 1 to about 4.

Preferably, $R^2$ and $R^3$ are methyl or ethyl groups.

Preferably, m is 2 or 3, i.e. an ethylene or propylene group.

Preferred amidoamines useful herein include stearamidopropyldimethylamine, stearamidopropyldiethylamine, stearamidoethyldiethylamine, stearamidoethyldimethylamine, palmitamidopropyldimethylamine, palmitamidopropyl-diethylamine, palmitamidoethyldiethylamine, palmitamidoethyldimethylamine, behenamidopropyldimethyl-amine, behenamidopropyldiethylmine, behenamidoethyldiethylamine, behenamidoethyldimethylamine, arachidamidopropyl-dimethylamine, arachidamidopropyldiethylamine, arachid-amidoethyldiethylamine, arachidamidoethyldimethylamine, and mixtures thereof.

Particularly preferred amidoamines useful herein are stearamidopropyldimethylamine, stearamidoethyldiethylamine, and mixtures thereof.

Commercially available amidoamines useful herein include:

stearamidopropyldimethylamine with tradenames LEXAMINE S-13 available from Inolex (Philadelphia Pennsylvania, USA) and AMIDOAMINE MSP available from Nikko (Tokyo, Japan), stearamidoethyldiethylamine with a tradename AMIDOAMINE S available from Nikko, behenamidopropyldimethylamine with a tradename INCROMINE BB available from Croda (North Humberside, England), and various amidoamines with tradenames SCHERCODINE series available from Scher (Clifton New Jersey, USA).

Acid may be any organic or mineral acid which is capable of protonating the amidoamine in the conditioner composition. Suitable acids useful herein include hydrochloric acid, acetic acid, tartaric acid, fumaric acid, lactic acid, malic acid, succinic acid, and mixtures thereof. Preferably, the acid is selected from the group consisting of acetic acid, tartaric acid, hydrochloric acid, fumaric acid, lactic acid and mixtures thereof.

The primary role of the acid is to protonate the amidoamine in the hair treatment composition thus forming a tertiary amine salt (TAS) in situ in the hair treatment composition. The TAS in effect is a non-permanent quaternary ammonium or pseudo-quaternary ammonium cationic surfactant.

Suitably, the acid is included in a sufficient amount to protonate more than 95 mole % (293 K) of the amidoamine present.

In conditioners for use in the invention, the level of cationic conditioning surfactant will generally range from 0.01 to 10%, more preferably 0.05 to 7.5%, most preferably 0.1 to 5% by total weight of cationic conditioning surfactant based on the total weight of the composition.

The Fatty Alcohol

The compositions of the invention comprise a fatty alcohol having a carbon-carbon chain length of from $C_8$ to $C_{22}$.

The combined use of fatty alcohols and cationic surfactants in conditioning compositions is preferred because this leads to the formation of a lamellar phase, in which the cationic surfactant is dispersed.

The fatty alcohol comprises from 8 to 22 carbon atoms, preferably 16 to 22, most preferably C16 to C18. Fatty alcohols are typically compounds containing straight chain alkyl groups. Preferably, the alkyl groups are saturated. Examples of preferred fatty alcohols include cetyl alcohol, stearyl alcohol and mixtures thereof. The use of these materials is also advantageous in that they contribute to the overall conditioning properties of compositions for use in the invention.

The level of fatty alcohol in conditioners for use in the invention will generally range from 0.01 to 10%, preferably from 0.1 to 8%, more preferably from 0.2 to 7%, most preferably from 0.3 to 6% by weight of the composition.

The weight ratio of cationic-surfactant to fatty alcohol is suitably from 1:1 to 1:10, preferably from 1:1.5 to 1:8, optimally from 1:2 to 1:5. If the weight ratio of cationic surfactant to fatty alcohol is too high, this can lead to eye irritancy from the composition. If it is too low, it can make the hair feel squeaky for some consumers.

Silicone

The compositions of the invention preferably contain, emulsified droplets of a silicone conditioning agent, for enhancing conditioning performance.

Suitable silicones include polydiorganosiloxanes, in particular polydimethylsiloxanes which have the CTFA designation dimethicone. Also suitable for use compositions of the invention (particularly shampoos and conditioners) are polydimethyl siloxanes having hydroxyl end groups, which have the CTFA designation dimethiconol. Also suitable for use in compositions of the invention are silicone gums having a slight degree of cross-linking, as are described for example in WO 96/31188. Preferably, the silicone is selected from the group consisting of dimethicone, dimethiconol, amodimethicone and mixtures thereof. Also preferred are blends of amino-functionalised silicones with dimethicones.

The viscosity of the emulsified silicone itself (not the emulsion or the final hair conditioning composition) is typically at least 10,000 cst at 25° C. the viscosity of the silicone itself is preferably at least 60,000 cst, most preferably at least 500,000 cst, ideally at least 1,000,000 cst. Preferably the viscosity does not exceed $10^9$ cst for ease of formulation.

Emulsified silicones for use in the shampoo compositions of the invention will typically have a D90 silicone droplet size in the composition of less than 30, preferably less than 20, more preferably less than 10 micron, ideally from 0.01 to 1 micron. Silicone emulsions having an average silicone droplet size (D50) of 0.15 micron are generally termed microemulsions.

Silicone particle size may be measured by means of a laser light scattering technique, for example using a 2600D Particle Sizer from Malvern Instruments.

Examples of suitable pre-formed emulsions include Xiameter MEM 1785 and microemulsion DC2-1865 available from Dow Corning. These are emulsions/microemulsions of dimethiconol. Cross-linked silicone gums are also available in a pre-emulsified form, which is advantageous for ease of formulation.

A further preferred class of silicones for inclusion in shampoos and conditioners of the invention are amino functional silicones. By "amino functional silicone" is meant a silicone containing at least one primary, secondary or tertiary amine group, or a quaternary ammonium group. Examples of suitable amino functional silicones include: polysiloxanes having the CTFA designation "amodimethicone". A preferred amodimethicone is commercially available from Dow Corning as DC 7134.

Specific examples of amino functional silicones suitable for use in the invention are the aminosilicone oils DC2-8220, DC2-8166 and DC2-8566 (all ex Dow Corning).

Suitable quaternary silicone polymers are described in EP-A-0 530 974. A preferred quaternary silicone polymer is K3474, ex Goldschmidt.

Also suitable are emulsions of amino functional silicone oils with non ionic and/or cationic surfactant.

Pre-formed emulsions of amino functional silicone are also available from suppliers of silicone oils such as Dow Corning and General Electric. Specific examples include DC939 Cationic Emulsion and the non-ionic emulsions DC2-7224, DC2-8467, DC2-8177 and DC2-8154 (all ex Dow Corning).

The total amount of silicone is preferably from 0.1 wt % to 10% wt of the total composition more preferably from 0.1 wt % to 5 wt %, most preferably 0.5 wt % to 3 wt % is a suitable level.

The Diester Quat

The inventive compositions comprise at least one ester quat, preferably of the structure shown below (I):

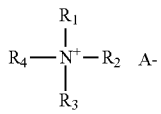

R3 and R4 are —X—O—CO—R5

Wherein, the radicals R1, R2 each independently of each other can be identical or different.

The radicals R1, R2 represent:

a branched or unbranched alkyl radical having 1 to 4 carbon atoms, preferably selected from the group selected from methyl, ethyl, propyl, iso-propyl, butyl, tert-butyl or iso-butyl, more preferably methyl, ethyl, propyl, and iso-propyl and most preferably methyl.

R3 and R4 are represented by —X—O—CO—R5, wherein:

X is a branched or unbranched alkyl group having 1 to 4 carbon atoms, preferably selected from methyl, ethyl, propyl, iso-propyl, butyl, tert-butyl or iso-butyl, more preferably ethyl, propyl or isopropyl and most preferably selected from ethyl and isopropyl.

R5 is selected from a saturated branched or unbranched, an unsaturated branched or unbranched, or a cyclic saturated or unsaturated alkyl radical, each having 6 to 30, preferably 12 to 24, more preferably 14 to 20 carbon atoms and which may contain a hydroxyl group.

R5 is preferably selected from a saturated or unsaturated branched alkyl radical, more preferably a saturated branched alkyl radical.

A is a physiologically compatible organic or inorganic anion. A is selected from the halide ions, fluoride, chloride, bromide, iodide, sulfates of the general formula $RSO_3^-$, wherein R is a saturated or unsaturated alkyl radical having 1 to 4 carbon atoms, with anionic radicals of organic acids such as maleate, fumarate, oxalate, tartrate, citrate, lactate or acetate. Preferred sulphates are methosulphate and ethosulphate. Most preferably, $A^-$ is selected from chloride, ethosulphate or methosulphate.

In a preferred embodiment, R3 and R4 have —X— that is selected from ethyl and isopropyl, R5 has chains selected from i) branched, saturated chains with a chain length of C18 or C16 and ii) unbranched, unsaturated or saturated chains, with a chain length of C18 or C16.

Examples of such compounds are preferably Dioleoylisopropyl Dimonium methosulfate, Dioleoylisopropyl Dimonium Chloride, Dipalmoylisopropyl Dimonium methosulfate, Dipalmoylisopropyl Dimonium Chloride, bis (Isostearoyl/oleoyl isopropyl) Dimonium methosulfate, bis (Isostearoyl/oleoyl isopropyl) Dimonium chlorides.

A highly preferred compound carries the name bis (Isostearoyl/oleoyl isopropyl) Dimonium methosulfate and is designated by the INCI nomenclature as Quaternium-98 and is commercially available under the name Varisoft® EQ 100 from Evonik. A further preferred compound is available under the name Varisoft® EQ 65 also from Evonik.

The esterquats corresponding to formula (I) are present in the inventive compositions in amounts of from 0.1 to 5 wt %, preferably 0.1 to 2, more preferably 0.5 to 1.5, even more preferably 0.5 to 1.2, most preferably 0.6 to 1 wt % based on the total weight of the composition.

Further Ingredients

The composition according to the invention may comprise any of a number of ingredients which are common to conditioning compositions Other ingredients may include viscosity modifiers, preservatives, colouring agents, polyols such as glycerine and polypropylene glycol, chelating agents such as EDTA, antioxidants such as vitamin E acetate, fragrances, antimicrobials and sunscreens. Each of these ingredients will be present in an amount effective to accomplish its purpose.

Generally these optional ingredients are included individually at a level of up to about 5% by weight of the total composition.

Preferably, compositions of this invention also contain adjuvants suitable for hair care. Generally such ingredients are included individually at a level of up to 2%, preferably up to 1%, by weight of the total composition.

Among suitable hair care adjuvants, are:

(i) natural hair root nutrients, such as amino acids and sugars. Examples of suitable amino acids include arginine, cysteine, glutamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose. These may be added singly or in the form of, e.g. fruit extracts.

(ii) hair fibre benefit agents. Examples are:

ceramides, for moisturising the fibre and maintaining cuticle integrity. Ceramides are available by extraction from natural sources, or as synthetic ceramides and pseudoceramides. A preferred ceramide is Ceramide II, ex Quest. Mixtures of ceramides may also be suitable, such as Ceramides LS, ex Laboratoires Serobiologiques.

free fatty acids, for cuticle repair and damage prevention. Examples are branched chain fatty acids such as 18-methyleicosanoic acid and other homologues of this series, straight chain fatty acids such as stearic, myristic and palmitic acids, and unsaturated fatty acids such as oleic acid, linoleic acid, linolenic acid and arachidonic acid. A preferred fatty acid is oleic acid. The fatty acids may be added singly, as mixtures, or in the form of blends derived from extracts of, e.g. lanolin.

Mixtures of any of the above active ingredients may also be used.

In a second aspect there is provided a method for the manufacture of a conditioning composition according to the first aspect. The method comprising forming a conditioning gel phase which comprises a cationic surfactant and a fatty material and, separately forming a solution of the hydrophobically modified polymer, optionally with a cationic surfactant, which, if present, is added to the water first.

The two mixtures are then added to one another before the remaining ingredients are added to form the conditioning composition.

Preferably, the extra ingredients include perfumes, thickeners and preservatives.

The invention will now be illustrated by the following non-limiting Examples:

EXAMPLES

The invention will now be illustrated by the following non-limiting Examples:

Example 1: Compositions for Treatment of Hair Prior to Microcapsule Deposition Analysis Three hair conditioner formulations were used to treat hair. Composition A is a comparative composition, whilst 1 and 2 are in accordance with the invention. The compositions are given in Table 1.

TABLE 1

Compositions of Conditioners A, B, and C

| INCI | Active Level | A | 1 | 2 |
|---|---|---|---|---|
| Bis(Isotearoyl/Oleoyllsoproypl) Dimonium Methosulfate (Varisoft EQ100) | 100 | 0 | 0.6 | 0 |
| Distrearoylethyl Dimonium Chloride (Varisoft EQ65) | 65 | 0 | 0 | 1.23 |
| Behentrimonium Chloride | 70 | 2.29 | 1.43 | 1.14 |
| Cetearyl Alcohol | 100 | 3.2 | 3.2 | 3.2 |
| Dimethicone 600K and Amodimethicone 2000 nm | 70 | 3.57 | 3.57 | 3.57 |
| Encapsulated perfume (ex IFF), with polyurea shell | 100 | 0.91 | 0.91 | 0.91 |
| Preservatives | 100 | 0.5 | 0.5 | 0.5 |
| Water | 100 | To 100 | To 100 | To 100 |

Formulations were made by adding the cationic surfactants to the fatty alcohol and stirring at 85° C. Gradually this mixture was added to water, typically at 55° C., such that the mixture temperature was 60° C. This temperature was maintained for 30 minutes with stirring. The mixture was then cooled towards ambient by adding more water, and adding remaining ingredients, and using external cooling if required, and stirred.

Example 2: Treatment of Hair with Compositions A, 1, and 2 and Encap Deposition Measurements in Accordance with the Invention The hair used was dark brown European hair, in switches of 0.25 g weight and 2 inch length.

The hair was treated with Compositions A, 1 and 2 as follows:—

Hair was first treated with a cleansing shampoo using the following method:—

The hair fibres were held under running water for 30 seconds, shampoo applied at a dose of 0.1 ml of shampoo per 1 g of hair and rubbed into the hair for 30 seconds. Excess lather was removed by holding under running water for 30 seconds and the shampoo stage repeated. The hair was rinsed under running water for 30 seconds.

The wet hair was then treated with Conditioner A or B or C using the following method:—Conditioner was applied to the wet hair at a dose of 0.2 g of conditioner per 1 g of hair and massaged into the hair for 1 minute. The hair was rinsed under running water for 1 minute and excess water removed. Hair was dried overnight at room temperature.

5 replicates hair switches were prepared for each conditioner. Each hair switch was cut into a vial, weighed and the required amount of solvent added and extracted for 1 hour. Each extract was pipetted into a 96-well micro litre plate for fluorescence spectrometry analysis along with a set of calibration standards with deposition efficiency range from 100% to 3%.

Microcapsule deposition efficiency measured on hair switches treated with Conditioners A, 1 and 2 are shown in Table 2.

TABLE 2

Microcapsule deposition efficiency on hair switches treated with Conditioners A, 1 and 2.

| Example | Microcapsule deposition (%) | Standard deviation/significance |
|---|---|---|
| A | 18.0 | 1.7 |
| 1 | 24.3 | 1.0 |
| 2 | 20.7 | 1.5 |

It will be seen that hair treated with Conditioners 1 and 2, in accordance with the invention, deposit higher levels of encapsulated benefit agent onto hair than comparative example A.

The invention claimed is:

1. A hair treatment composition consisting of:
   a) a conditioning base comprising:
      i) 0.01 to 10 wt % a cationic conditioning surfactant having from 16 to 32 carbon atoms;
      ii) 0.01 to 10 wt % a fatty alcohol having from 8 to 22 carbon atoms;
   b) from 0.1 to 10 wt % of a microcapsule in which a core comprising benefit agent is encapsulated in a polymeric shell, wherein the benefit agent is a perfume, cosmetic active ingredient, antimicrobial agent, antidandruff agent, moisturizer, conditioning agent, sunscreen agent, physiological coolant, emollient oils, or mixtures thereof;
   c) from 0.1 to 5 wt % of a diesterquat, wherein the diesterquat is defined by formula (I):

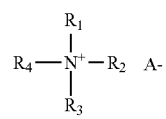

(I)

wherein radicals $R_1$ and $R_2$ each independently of each other can be identical or different and are a branched or unbranched alkyl radical having 1 to 4 carbon atoms;

$R_3$ and $R_4$ are represented by —X—O—CO—$R_5$, wherein X is a branched or unbranched alkyl group having 1 to 4 carbon atoms; and $R_5$ is selected from a saturated branched or unbranched, an unsaturated branched or unbranched, or a cyclic saturated or unsaturated alkyl radical, each having 6 to 30 carbon atoms and which may contain a hydroxyl group; and A- is a physiologically compatible organic or inorganic anion;

d) optionally 0.1 to 10 wt % of a silicone selected from the group consisting of dimethicone, dimethiconol, amodimethicone and mixtures thereof;
   e) optionally an ingredient selected from the group consisting of a viscosity modifier, preservative, colouring agent, chelating agent, fragrance, and antioxidant;

f) optionally an adjuvant; and g) water.

2. The hair treatment composition of claim 1, wherein the benefit agent is a perfume.

3. The composition of claim 1, wherein $R_5$ is selected from a saturated or unsaturated branched alkyl radical.

4. The composition of claim 1, wherein X is selected from ethyl or isopropyl, $R_5$ has chains selected from i) branched, saturated chains with a chain length of C18 or C16, or ii) unbranched, unsaturated or saturated chains, with a chain length of C18 or C16.

5. The composition of claim 1, wherein the radicals $R_1$ and $R_2$ of the diesterquat are independently selected from the group consisting of methyl, ethyl, propyl, iso-propyl, butyl, tert-butyl and iso-butyl.

6. The composition of claim 1, wherein X is selected from the group consisting of methyl, ethyl, propyl, iso-propyl, butyl, tert-butyl and iso-butyl.

7. The composition of claim 1, wherein the diesterquat is selected from bis (isostearoyl/oleoyl isopropyl) dimonium methosulfate or dioleoylisopropyl dimonium methosulfate.

8. The composition of claim 1, wherein the diesterquat is present in an amount of from 0.5 to 1.2 wt % based on the total weight of the composition.

9. The composition of claim 1, wherein the microcapsule is an aminoplast resin selected from polyurea formed by reaction of polyisocyanates with material selected from polyamines, polyimines or mixtures thereof.

10. The composition of claim 9, wherein the microcapsule has a polyurea shell.

11. A method of treating hair comprising applying to the hair the composition of claim 1.

12. The composition of claim 1, wherein $R_5$ is selected from a saturated branched or unbranched, an unsaturated branched or unbranched, or a cyclic saturated or unsaturated alkyl radical, each having 12 to 24 carbon atoms.

13. The composition of claim 1, wherein $R_5$ is selected from a saturated branched or unbranched, an unsaturated branched or unbranched, or a cyclic saturated or unsaturated alkyl radical, each having 14 to 20 carbon atoms.

14. The composition of claim 5, wherein radicals $R_1$ and $R_2$ of the diesterquat are independently selected from the group consisting of methyl, ethyl, propyl, and iso-propyl.

15. The composition of claim 6, wherein X is selected from the group consisting of ethyl, propyl and isopropyl.

16. The composition of claim 6, wherein X is ethyl or isopropyl.

* * * * *